(12) United States Patent
Roesler et al.

(10) Patent No.: US 10,398,523 B2
(45) Date of Patent: Sep. 3, 2019

(54) PACKAGING SLEEVE FOR MEDICAL PURPOSES

(71) Applicants: Peter Roesler, Wangen (DE); Thiemo Roesler, Wangen-Neuravensburg (DE)

(72) Inventors: Peter Roesler, Wangen (DE); Thiemo Roesler, Wangen-Neuravensburg (DE)

(73) Assignee: Roesler IP GmbH (DE)

( * ) Notice: Subject to any disclaimer, the term of this patent is extended or adjusted under 35 U.S.C. 154(b) by 163 days.

(21) Appl. No.: 15/285,881

(22) Filed: Oct. 5, 2016

(65) Prior Publication Data
US 2017/0095308 A1    Apr. 6, 2017

(30) Foreign Application Priority Data
Oct. 6, 2015  (DE) .......................... 10 2015 012 898

(51) Int. Cl.
| A61B 50/30 | (2016.01) |
| A61C 8/00 | (2006.01) |
| A61B 17/86 | (2006.01) |
| B65D 81/05 | (2006.01) |
| A61B 50/00 | (2016.01) |

(52) U.S. Cl.
CPC ............ *A61B 50/30* (2016.02); *A61B 17/865* (2013.01); *A61C 8/0087* (2013.01); *B65D 81/05* (2013.01); *A61B 2050/005* (2016.02); *A61B 2050/0051* (2016.02); *A61B 2050/0066* (2016.02); *A61B 2050/0072* (2016.02)

(58) Field of Classification Search
CPC .. A61C 8/0087; B65D 81/05; B65D 77/0486; A61B 50/30; A61B 17/865; A61B 2050/005; A61B 2050/0051; A61B 2050/0066; A61B 2050/0072

USPC ....................... 206/438, 368, 63.5, 521, 446; 220/521–200, 243, 234, 801, 254.1, 789, 220/254.7, 23.83, 23.86–23.89; 215/355
See application file for complete search history.

(56) References Cited

U.S. PATENT DOCUMENTS

| 4,139,311 | A | * | 2/1979 | Lorscheidt | ............. A45D 40/02 215/341 |
| 4,856,668 | A | * | 8/1989 | Pfefferkorn | ........ B65D 39/0023 215/329 |
| 5,275,287 | A | * | 1/1994 | Thompson | ......... B65D 41/0421 215/341 |
| 5,356,006 | A | | 10/1994 | Alpern et al. | |
| 5,368,160 | A | * | 11/1994 | Leuschen | ............. A61C 8/0087 206/339 |
| 5,538,428 | A | | 7/1996 | Staubli | |

(Continued)

FOREIGN PATENT DOCUMENTS

EP    2279708    2/2011

*Primary Examiner* — Chun Hoi Cheung
(74) *Attorney, Agent, or Firm* — Cohen & Grigsby, P.C.

(57) ABSTRACT

Packaging sleeve for medical purposes for storing sterile objects (25, 45), consisting of at least one outer sleeve (2) that is open at one end and can be sealed with a sealing closure (10) and has an inner sleeve (12) accommodated in it with a clamping effect, wherein the inner sleeve (12) is accommodated in a clamping seating in a receiving opening (15) in the sealing closure (10) on the bottom side of the outer sleeve (2) and the clamping seat thereby formed presses the sealing ribs (7, 55, 56, 59) arranged on the outside circumference of the sealing closure (10) against the inside of the outer sleeve (2) under increased contact pressure (FIG. 1).

6 Claims, 11 Drawing Sheets

(56) References Cited

U.S. PATENT DOCUMENTS

| | | | | |
|---|---|---|---|---|
| 5,558,230 | A * | 9/1996 | Fischer | A61C 8/0087 |
| | | | | 206/570 |
| 5,622,500 | A * | 4/1997 | Niznick | A61C 8/0048 |
| | | | | 206/63.5 |
| 5,690,246 | A * | 11/1997 | Anderson | B01L 3/50825 |
| | | | | 206/446 |
| 6,189,755 | B1 * | 2/2001 | Wakefield | B60N 3/103 |
| | | | | 220/23.89 |
| 6,217,332 | B1 * | 4/2001 | Kumar | A61C 8/0087 |
| | | | | 206/368 |
| 6,247,932 | B1 * | 6/2001 | Sutter | A61C 8/0087 |
| | | | | 206/368 |
| 6,280,192 | B1 | 8/2001 | Groll | |
| 6,594,971 | B1 | 7/2003 | Addy et al. | |
| 6,955,258 | B2 * | 10/2005 | Howlett | A61C 8/0087 |
| | | | | 206/368 |
| 7,147,192 | B2 * | 12/2006 | Kong | B60N 3/108 |
| | | | | 248/311.2 |
| 8,002,547 | B2 * | 8/2011 | Porter | A61C 8/0001 |
| | | | | 433/173 |
| 9,265,579 | B2 * | 2/2016 | Richart | A61B 17/865 |
| 9,585,727 | B2 * | 3/2017 | Richart | A61B 50/30 |
| 2009/0065387 | A1 | 3/2009 | Bammerlin | |
| 2014/0042050 | A1 * | 2/2014 | Richart | A61B 17/865 |
| | | | | 206/438 |

* cited by examiner

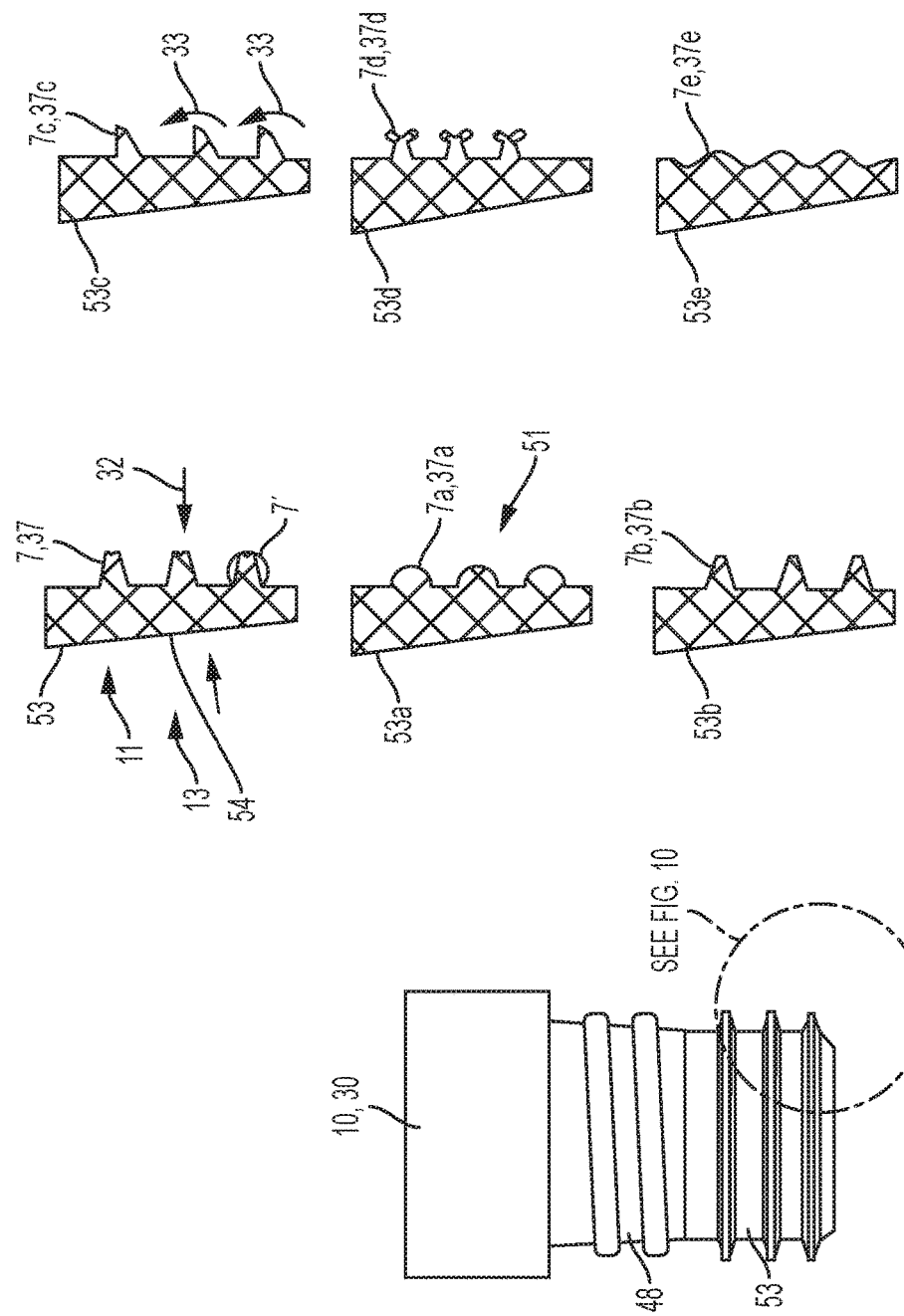

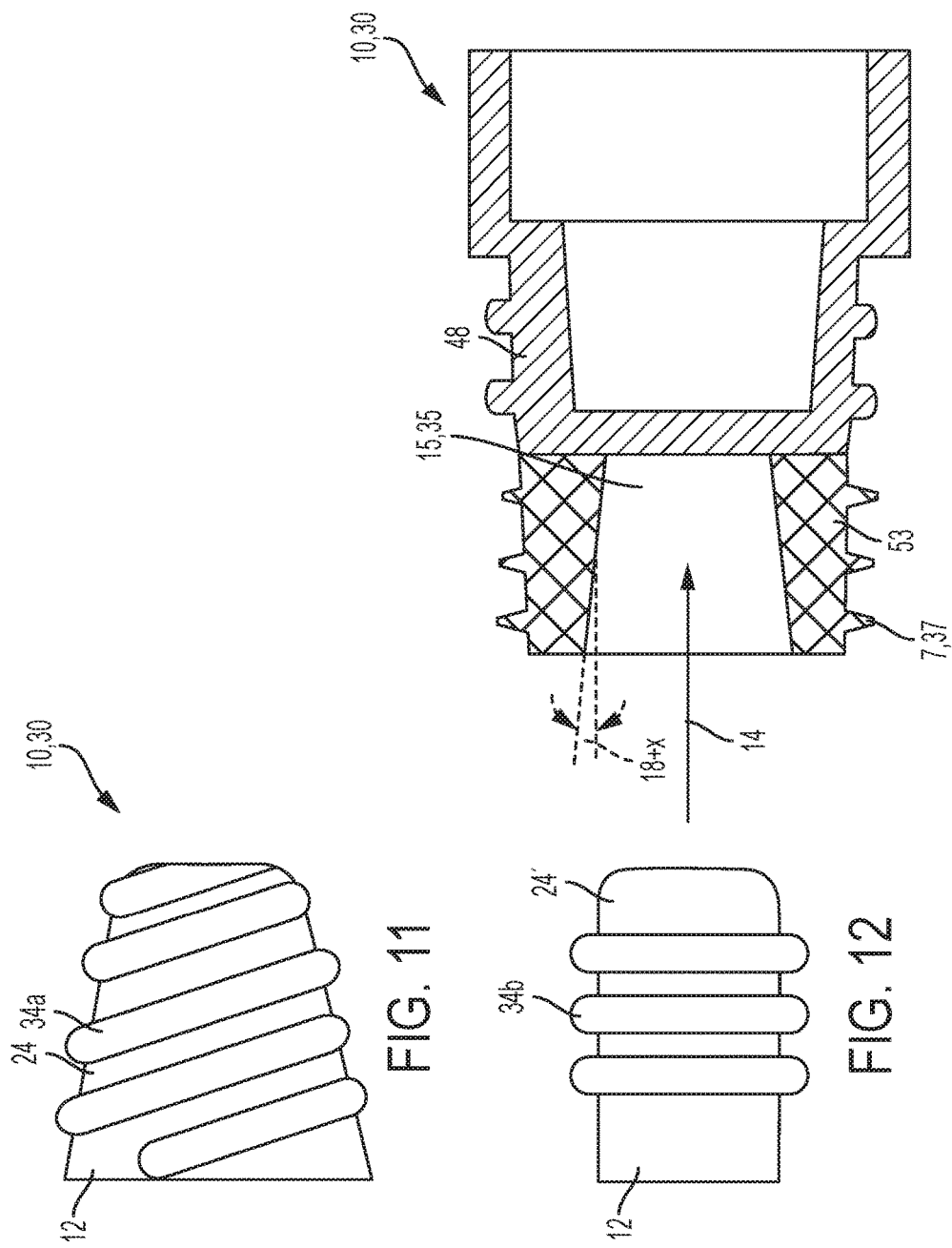

PACKAGING SLEEVE FOR MEDICAL PURPOSES

CROSS-REFERENCE TO RELATED APPLICATION

This application claims the benefit of priority of Application No. 102015012898.1, filed in Germany on Oct. 6, 2015, the right of priority of which is claimed in the present application and the subject matter of which is incorporated herein by reference in its entirety.

BACKGROUND OF THE INVENTION

Field of the Invention

The invention relates to a packaging sleeve for medical purposes for storing sterile objects according to the preamble of patent claim 1.

An important factor in the storage and presentation of medical objects and surgical instruments in the operating room is to ensure the sterility of the object or instrument arranged in a packaging sleeve.

The subject matter of DE 693 19 704 T2 relates to a sterilized packaging for surgical instruments, where the packaging consists of an outer sheath for example a polyethylene bag, which is sealed with a pull strip. Several layers of foam with closed cells are arranged inside the bag. The various instruments and devices for use in a surgical procedure are arranged in each of the layers of foam with closed cells. The container with the foam layers is surrounded by a first sheath. This sheath is designed to be sterile, and a second sterile sheath encloses the first sterile sheath.

Such a bag system with instruments embedded in the foam in it has the disadvantage that its imperviousness cannot be guaranteed. Its imperviousness is ensured only by adhesive strips and the respective seals. It is therefore also not suitable for holding sterile liquids because the imperviousness of the packaging cannot be ensured.

DE 699 38 259 C2 describes a sterile packaging for flexible endoscopes. It consists of a pocket with a front film made of a clear impermeable polymer and a rear film made of a semipermeable material, such as a polyethylene nonwoven.

An adhesive seal covers the outside edges of the front film and forms a sealed interior. Accordingly, with this bag packaging, there is again the disadvantage that only the imperviousness is to be ensured by sealing surfaces, in the area of adhesive films. However, this is not enough for certain intended applications, in which increased demands are made of the imperviousness.

Discussion of the Prior Art

US 2014/0042050 A1 describes a packaging sleeve for medical purposes for storing sterile objects, consisting of a sealing closure, which can be screwed onto the outer sleeve of the packaging, which is open at one end.

A second packaging sleeve, which is offset by 180°, can be inserted into and stored in the outer sleeve with a clamping effect in the sealing closure.

The object to be protected from contamination is situated in the interior of the inner sleeve, which can be sealed with a similar sealing closure.

One disadvantage of this known packaging is that it is impossible to ensure that the respective seal is also designed to be tight enough simply by screwing the sealing closure onto the outer sleeve.

Another disadvantage is that the object to be protected from contamination is not clamped in the inner sleeve.

Instead it is freely displaceable there. Removal of such an object is therefore difficult, because the sealing closure must be unscrewed from the inner sleeve for the purpose of removal, so that the object stored there loosely can fall out accidentally.

Another disadvantage of US 2014/0042050 A1 is that it is impossible to ensure a reliable seal on the outer sleeve because the inner sleeve accommodated in the bottom area of the sealing closure does not result in tightening of the seal between the sealing closure and the interior of the outer sleeve.

Another disadvantage is that the sealing closure also does not ensure reliable sealing for the closure of the inner sleeve because, even with this sealing closure, there is still the problem that there is no radial widening of the sealing ribs of this sealing closure by an expansion object clamped in the bottom area of the sealing closure.

SUMMARY OF THE INVENTION

The object of the invention based on US 2014/0042050 A1 is therefore to improve upon a packaging sleeve for medical purposes for storage of sterile objects, so that the handling of the sterile objects to be stored can be made much simpler and more reliable and so that there will always be an adequate seal of the sealing closures on the outer sleeve and the inner sleeve.

To achieve the object formulated here, the invention is characterized by the technical teaching of the independent claim 1.

In the manner of US 2014/0042050 A1, the present invention provides that there are two sleeves inserted coaxially, one inside the other, wherein one inner sleeve is rotated by 180° in its position in its accommodation in the interior of the outer sleeve, and the inner sleeve is accommodated with its bottom side part in the bottom side receptacle of the sealing closure for the closure of the outer sleeve.

In the same way as described in US 2014/0042050 A1, simplified handling is thus possible because, in a preferred exemplary embodiment, the double packaging sleeve consisting of two inner and outer sleeves inserted coaxially, one inside the other, forming a seal and screwed together, is first opened outside of the sterile operating room by an operator, and the inner sleeve is pulled out of the outer sleeve.

While still closed, the inner sleeve thereby freed, with the medical object inserted into it, is introduced into the operating room through an airlock and then handed over to the operating-room nurse and/or surgeon.

The operating-room nurse and/or the surgeon then open(s) the inner sleeve, which is still sealed, under sterile conditions, wherein the sealing closure of the inner sleeve is unscrewed and removed. The medical object stored in the inner sleeve is then introduced into the operating area under sterile conditions and used in the human or animal body.

In a first embodiment, the object to be held is stored loosely in the inner sleeve and can be removed without touching the object, by just shaking the inner sleeve, which has been opened.

The object of the present invention is therefore to improve upon a packaging for medical purposes, for storing sterile objects, so that significantly higher imperviousness requirements can be met, and better protection is provided against contamination due to touch contact.

The invention is first directed to a hard packaging and avoids the types of bag packaging referenced above. The invention therefore claims a packaging sleeve that is open at one end and can be closed with a sealing closure.

Such a sealing closure is essentially comparable to a sealing plug or stealing stopper, which is screwed, locked, pushed or otherwise connected securely and with a seal to the open end of the packaging sleeve, either in or on the end of the packaging sleeve, which is open at one end, so that the packaging sleeve is sealed by such a sealing closure.

When using such sealing closures, it is known that one or more sealing ribs may be arranged on the outside circumference of such a stopper-like sealing closure, and these sealing ribs are in contact with the inside circumference of the packaging sleeve when the sealing closure is pushed or screwed into the end of the packaging sleeve, which is open at one end, resulting in an additional seal. Such sealing closures are known in general for tubes for storing tablets.

Thus, however, increased demands regarding the imperviousness of such a sealing closure cannot be met with sealing ribs arranged on the outside circumference.

Description of a First Specific Embodiment

The Invention Therefore Provides That the sealing seat of the sealing ribs of the sealing closure on the inside circumference of the packaging sleeve is improved by the fact that the sealing closure has a receiving opening, which is open at one end and is preferably designed to be either cylindrical or with a conical enlargement, and an expansion element can be inserted into and/or screwed into this receiving opening in the axial direction, being held by an annular wall formed by the receiving opening with a clamping seat.

As soon as the sealing closure has been screwed onto the recess, which is open at one end, in the packaging sleeve and thereby pushed into the packaging sleeve, the expansion element, which is also arranged in the interior of the packaging sleeve, penetrates into the axial recess, which is open at one end in the bottom area of the sealing closure and thereby deforms the annular wall radially outward, so that the sealing ribs arranged on the outside circumference of the elastomerically deformable annular wall are pressed against the inside of the outer sleeve under an increased contact pressure.

Thus, with the technical teaching of claim 1, the sealing seat of a sealing closure in a packaging sleeve that is open at one end is improved in such a manner that an expansion element, which is arranged in the interior of the packaging, penetrates into the receiving opening in the sealing closure on the bottom side, which is open at one end, on insertion, screwing in or otherwise introducing the sealing closure into the packaging sleeve, displacing the walls of the sealing closure radially outward, and pressing the sealing ribs, which are arranged on the outside circumference of these walls, against the inside wall of the outer sleeve under an increased sealing pressure and contact pressure.

Such an expansion element may be an inner sleeve to be described later or a sterile object, in particular also a surgical instrument or some other device that must be handled under sterile conditions and is suitable for penetrating with part of its body into the opening in the sealing closure, which is open on the bottom end and thereby causing it to expand radially outward with a clamping effect.

In a first embodiment, it is provided that the expansion element is inserted in a straight line axially into the receiving space in the sealing stopper, where it is clamped with elastomeric deformation of the sealing stopper.

In a second embodiment, it is provided that the expansion element penetrates with a twisting movement and/or a twist-push movement into the receiving opening at the sealing closure, where it is secured by means of friction locking. To this end, thread-type projections, nubs or threaded strips may be molded onto the inside circumference of the receiving opening in the sealing closure, where they cooperate with the respective thread-type projections, nubs, threaded strips or smooth surfaces on the outside circumference of the inner sleeve.

If a twist-clamp connection is also selected according to the second embodiment instead of a plug-clamp connection, which acts only in the axial direction according to a first embodiment, then the inner sleeve can be removed from the sealing stopper with a controlled twisting movement. This will be explained below with reference to the drawings in FIGS. 11 through 13.

In the simplest embodiment of the invention, the packaging sleeve for medical purposes for storing a sterile object thus consists of an outer sleeve, which is open at one end and has a sealing closure, wherein the expansion means should be designed to penetrate with one part into the bottom-side opening of the sealing closure, which is open at one end where it has a clamping effect and optionally undergoes elastomeric deformation when the sealing closure is placed on the packaging sleeve. This results in radial widening of the wall of the sealing closure, so that the sealing ribs arranged on the outside circumference of the sealing closure are pressed against the inside wall of the packaging sleeve under an elevated contact pressure.

This simplified embodiment thus describes only a packaging sleeve with a sealing closure and a part of an expansion means engaging in the receiving opening that is open at one end on the bottom side, wherein the expansion means are formed either by the object itself that is to be held or by the bottom side of an inner sleeve.

The expansion means are accommodated with a clamping effect in the receiving opening of the sealing closure when the sealing closure is screwed into the outer sleeve and there is elastic deformation of the receiving opening on the bottom side radially outward in the sealing closure, so that the sealing ribs arranged on the outside circumference of the sealing closure are pressed against the inside of the outer sleeve under an increased contact pressure. The expansion element is thus formed either by the walls of the inner sleeve or—if the inner sleeve is omitted—by the object itself to be held.

For the sake of a simpler description, it is assumed below that the inner sleeve with its bottom part is the expansion element for the receiving opening in the sealing closure of the outer sleeve, although the invention is not limited to this embodiment.

The advantage of this measure is that it permits easy removal of the inner sleeve; the outer sealing closure is unscrewed or pulled out of the outer sleeve, wherein the inner sleeve, which is held in the interior of the outer sealing closure, remains clamped because of its clamping seating in the sealing closure, so that when the sealing closure is pulled out or unscrewed at the same time, the inner sleeve, which is held there by the sealing closure, is also pulled out of the outer sleeve.

The sealing closure of the outer sleeve therefore serves as a sterile hold for handling of the inner sleeve arranged in the interior of the outer sleeve, and there is no need to touch by hand the inner sleeve that is accommodated with a clamping effect in the sealing closure.

The invention thus relates to a packaging sleeve consisting of two sleeves inserted coaxially one into the other, namely an outer sleeve that has a larger diameter and can be closed by a sealing closure and an inner sleeve with a smaller diameter that is accommodated in the interior of the outer sleeve and can be closed by a second sealing closure at its end.

Thus, in this embodiment, two different sleeves are inserted, one inside the other, because in the interior of the outer sleeve that can be closed with the first sealing closure, the inner sleeve that can be closed with a second sealing closure is accommodated in a clamping fit in the receiving opening of the sealing closure of the outer sleeve on the bottom side.

The inner sleeve thus forms the expansion element for expansion of the sealing closure in the outer sleeve and the clamping seat thereby formed presses the sealing ribs arranged on the outer circumference of the sealing closure against the inside of the outer sleeve under increased contact pressure.

When in this embodiment a two-part packaging sleeve is provided with an inner sleeve and an outer sleeve, it is preferable if the inner sleeve retains the medical object to be held.

This yields substantial advantages in the transfer of such a medical object in the operating room:

In principle, the sealing closure, which seals the outer sleeve, is situated opposite the sealing closure arranged in the interior of the outer sleeve, supported on its bottom side and sealing the inner sleeve under an increased contact pressure.

To take out the object in the operating room, it is thus provided that the first sealing closure, which seals the outer sleeve, is pulled out or unscrewed from the outer sleeve, so that the inner sleeve, which is held in a clamping fit by the first sealing closure can be pulled out of the outer sleeve.

The surgical nurse holds the first sealing closure, which serves to close the outer sleeve in his/her hand and extends to the surgeon the inner sleeve, which is accommodated in a clamping fit in the first sealing closure and is still sealed by the second sealing closure.

The surgeon receives the inner sleeve with the second sealing closure still sitting on it and takes the second sealing closure out of the inner sleeve, so that the surgical element, instrument or object held in the clamping seating in the second sealing closure remains in the clamping seating on the second sealing closure, and the surgeon holds the second sealing closure in his hand until he can introduce the surgical instrument into the operating area having to touch the element, the object or the instrument.

Instead of holding the object that is to be held in the clamping seating in the inner sleeve, it is also possible to provide that the object is supported in a freely movable manner in the inner sleeve.

In the first case, touch-free manipulation of the object, element or instrument, which is held with a clamping effect in the clamping seat in the sealing closure of the inner sleeve.

In the sealing arrangement between the second sealing closure and the end of the inner sleeve, which is open at one end, it is ensured in a refinement of the invention that the object to be held is accommodating for example with its head area in the clamping seating in the elastically widenable opening of the second sealing closure at the bottom side of the inner sleeve so that even in this case due to the elastic widening of the receiving opening, the sealing ribs arranged on the outside circumference of the second sealing closure are pressed against the inside of the inner sleeve under an increased contact pressure.

Instead of the possibility that the object to be held in the inner sleeve itself acts as an expansion element for the receiving opening in the sealing closure of the inner sleeve, it is possible to provide in another embodiment that the expansion element is formed in the receiving opening of the inner sealing closure as a separate pressure piece.

The pressure piece is preferably designed to be conical and when the pressure piece is inserted axially into the receiving opening, which is also designed to be conical, the latter is widened radially. The axial longitudinal movement of the pressure piece is achieved by contact with the object held in a secure position in the inner sleeve at the end.

Description of a Second Embodiment

In a second embodiment of the present invention a modified embodiment in comparison with the embodiment according to FIGS. 1 to 13 is claimed, wherein the second embodiment—which is shown in particular in FIG. 15 and in the following figures—is characterized in that another sealing arrangement is provided for the sealing closure. For the same parts of the first exemplary embodiment according to FIGS. 1 to 13, the same reference numerals, explanations, features and advantages also apply to the parts of the second exemplary embodiment according to FIGS. 14 to 19.

This arrangement is characterized in that in comparison with the embodiment according to FIG. 1, the thread and the sealing ribs are interchanged, and furthermore, the second exemplary embodiment is characterized by an improved seal in that the bottom sleeve of the inner sleeve is connected to the sealing closure in a different sealing relationship than in the exemplary embodiment according to FIG. 1 by comparison.

In the embodiment according to the second design, the free open end of the outer sleeve forms a sealing sleeve that is open at the end and on whose inside circumference a novel sealing ring is now in contact, this sealing ring in turn sitting on the outside circumference of the newly formed sealing closure.

Due to the use of a sealing ring in combination with the sealing sleeve on the free open end of the inner sleeve, this yields a particularly advantageous seal, such as that which could not be achieved with the first exemplary embodiment.

The advantage of the second embodiment is that the sealing arrangement of the outer sleeve in combination with the sealing stopper is forced entirely against the end of the sealing stopper in the axial direction, i.e., is arranged on the outer axial end of the sealing stopper so that a better sealing effect and improved production against contamination are achieved.

The area where the seal is formed and the sealing ring is arranged is thus shifted as much as possible in the axial direction onto the stopper with the sealing closure. This yields the advantage that the internal sterility of the outer sleeve is ensured at all points.

If, in removal of the sealing closure, there happens to be unintentional contact of the inner surface of the outer sleeve, then this contamination is not introduced into the interior of the outer sleeve because any possible contamination cannot reach the inner surface of the outer sleeve. Thus, any contaminated surfaces are arranged at the greatest possible distance axially from the outer sleeve in order to prevent contamination of the outer sleeve on the inside.

The present invention also claims certain embodiments for the design of the seal between the sealing closure and the inside circumference of the outer sleeve.

In the exemplary embodiment referenced above, a seal applied to the outside circumference of the sealing closure and secured in position there is used. This sealing ring has sealing ribs of different shapes, namely one sealing rib on the front end and two sealing ribs facing radially outward, so that the sealing ring forms a seal in two directions orthogonal to one another, namely radially and axially.

It is also secured against twisting and secured positionally on the sealing closure against displacement in this way and is therefore "captive."

In a first embodiment, the securing of the position of the sealing ring on the stopper-type sealing closure is selected so that it sits on a cylindrical outside circumference of the sealing closure and forms a relatively great wall thickness in the direction of the conical inclination of the sealing closure toward the inside radially.

In another design, however, it may be provided that the wall thickness in the area of the sealing stopper is greatly reduced at the point where the sealing ring sits to ensure that a spring element is formed by the reduced wall thickness; this, combined with an outwardly directed radial pressure from the sealing closure, which acts on the inside circumference of the sealing ring, deforms the ring additionally outward in the radial direction and thereby increases and improves the sealing pressure and the sealing force on the inside circumference of the sealing sleeve in the area of the outer sleeve.

Thus an improved seal is achieved in that the sealing ring is designed as a spring element capable of transferred radial pressures from its inside circumference to the outside circumference.

In another embodiment, it is possible to provide for the sealing ring to be connected to the stopper-type sealing closure in one piece at the factory and therefore the previously defined wall thickness of the sealing ring is completely omitted. In this case the sealing ring according to the invention forms a wall of the sealing closure directly and is part of this wall.

It is thus capable of transferring the deforming force acting on the inside of the sealing closure directly outward radially to the seal, which is arranged there in the outward direction radially.

In addition to the three exemplary embodiments mentioned above, a fourth exemplary embodiment will now also be described, wherein it is provided that the inventive sealing ring is not in contact with a cylindrically shaped outer wall of the stopper-type sealing closure but instead this outer wall is formed with a conical taper in the axial direction.

More specifically, these are two different contact angles, wherein in the first contact area of the sealing ring a cylindrical contact face is formed and in a second contact area a conical contact face is formed.

This type of design of the contact faces has the advantage that the bracing force between the inner sleeve and the sealing closure is introduced at a specific defined axial location on the sealing ring and therefore a superior sealing effect is achieved and is introduced in concentrated form in a certain area of the seal.

The subject matter of the present invention is thus derived not only from the subject matter of the individual patent claims, but also from the combination of the individual patent claims with one another.

All the information and features disclosed in the documents including the abstract, in particular the three-dimensional design depicted in the drawings are hereby claimed as essential to the invention inasmuch they are novel individually or in combination in comparison with the prior art.

Inasmuch as individual subject matters are identified as being "essential to the invention" or "important," this does not mean that these subject matters need necessarily form the subject matter of an independent claim. This is determined only by the respective valid version of the independent patent claim.

BRIEF DESCRIPTION OF THE DRAWINGS

The invention is explained in greater detail below on the basis of drawings illustrating just one type of embodiment. Additional features that are essential to the invention and advantages of the invention are derived from the drawings and the description thereof.

They show:

FIG. 9 shows a side view of a sealing closure.

FIG. 10 shows schematically a detailed section through the sealing closure with six different diagrams of the design of the sealing ribs.

FIG. 11 shows a schematic diagram of a first profile design of the bottom side of the inner sleeve.

FIG. 12 shows a schematic diagram of a second profile design of the bottom side of the inner sleeve.

FIG. 13 shows schematic diagram of the penetration of the bottom side of the inner sleeve into the receiving opening of the sealing closure.

DESCRIPTION OF A PRESENTLY PREFERRED EMBODIMENT

Figure 1:
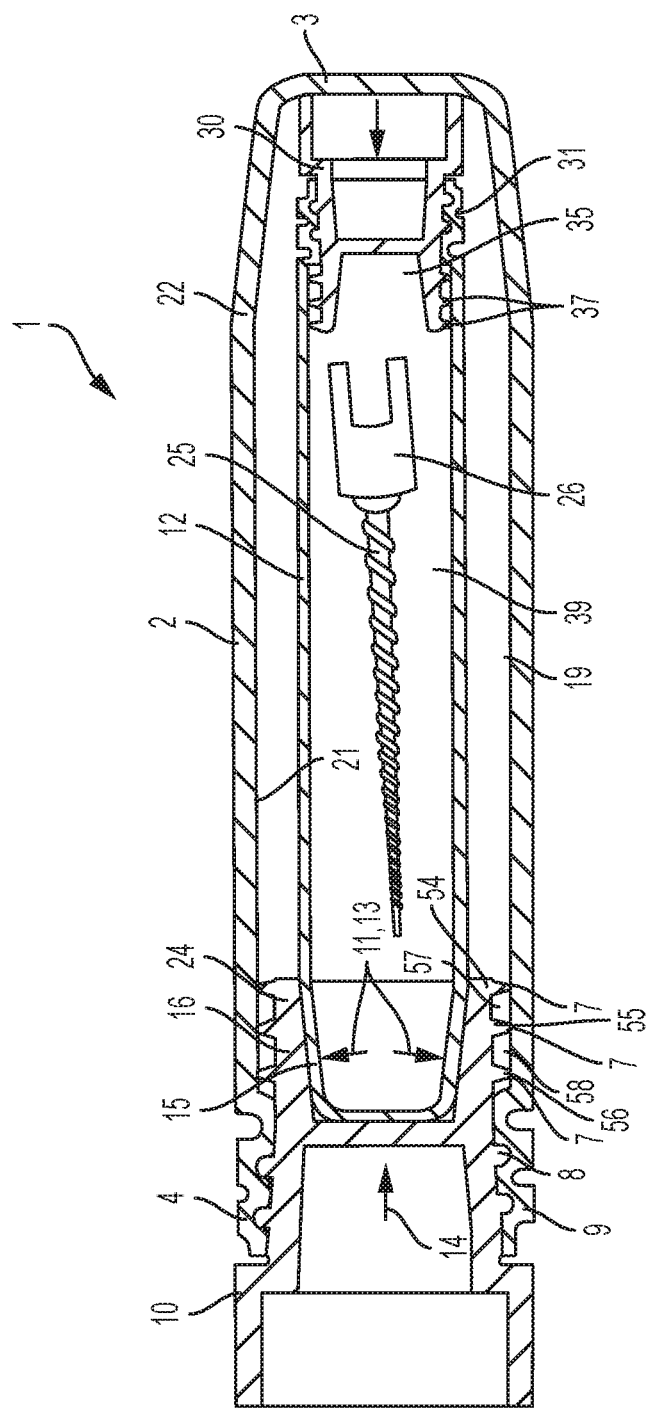
FIG. 1 shows a first embodiment of the invention in a longitudinal section.

With reference to FIGS. 1 through 5, the exemplary embodiment will be described first according to the technical teaching of the independent claim 1, wherein the packaging sleeve 1 consists of two packaging sleeves 2, 12 inserted coaxially one into the other.

The packaging sleeve 1 thus consists of a cylindrical outer sleeve 2 and a sealing closure 10, which closes the opening side 4 of the outer sleeve 2, as well as an inner sleeve 12 accommodated in the interior of the outer sleeve 2 and accommodated in the interior 19 in a position in which it is rotated by 180° and also has a sealing closure 30.

The sealing closure 10 on the outer sleeve has an outer thread 8, which cooperates with the respective inner thread 9 on the opening side 4 of the outer sleeve 2. The sealing closure 10 can be screwed into the opening side 4 of the outer sleeve 2 in this way.

A number of sealing ribs 7 arranged parallel to one another and arranged at an axial distance from the outer thread 8 are arranged on the outside circumference of the sealing closure 10 in the area of the elastomerically deformable annular wall 16 at the front axially. These sealing ribs are inclined toward the rear in the direction of insertion and are thus in sealing contact with the inside circumference 21 of the outer sleeve 2. The receiving opening 15 formed by the annular wall 16, open at one end, is designed as a conical inclination 17 having a cone angle 18.

The conical inclination 17 of the receiving opening 15 may be designed to be smooth or may also have a thread-type profile.

The opening side 4 of the outer sleeve 2 is offset by a shoulder 20 of a reduced diameter from the remaining interior 19 of the outer sleeve 2, and the bottom sleeve 22 has a conical constriction and is closed at the bottom. The bottom sleeve 22 is thus sealed by the bottom side 3.

The front end 5 of the opening side 4 is open and has a peripheral edge, which is stopped at the respective peripheral stop edge 6 on the circumference of the sealing closure 10 when screwed in.

Figure 2:
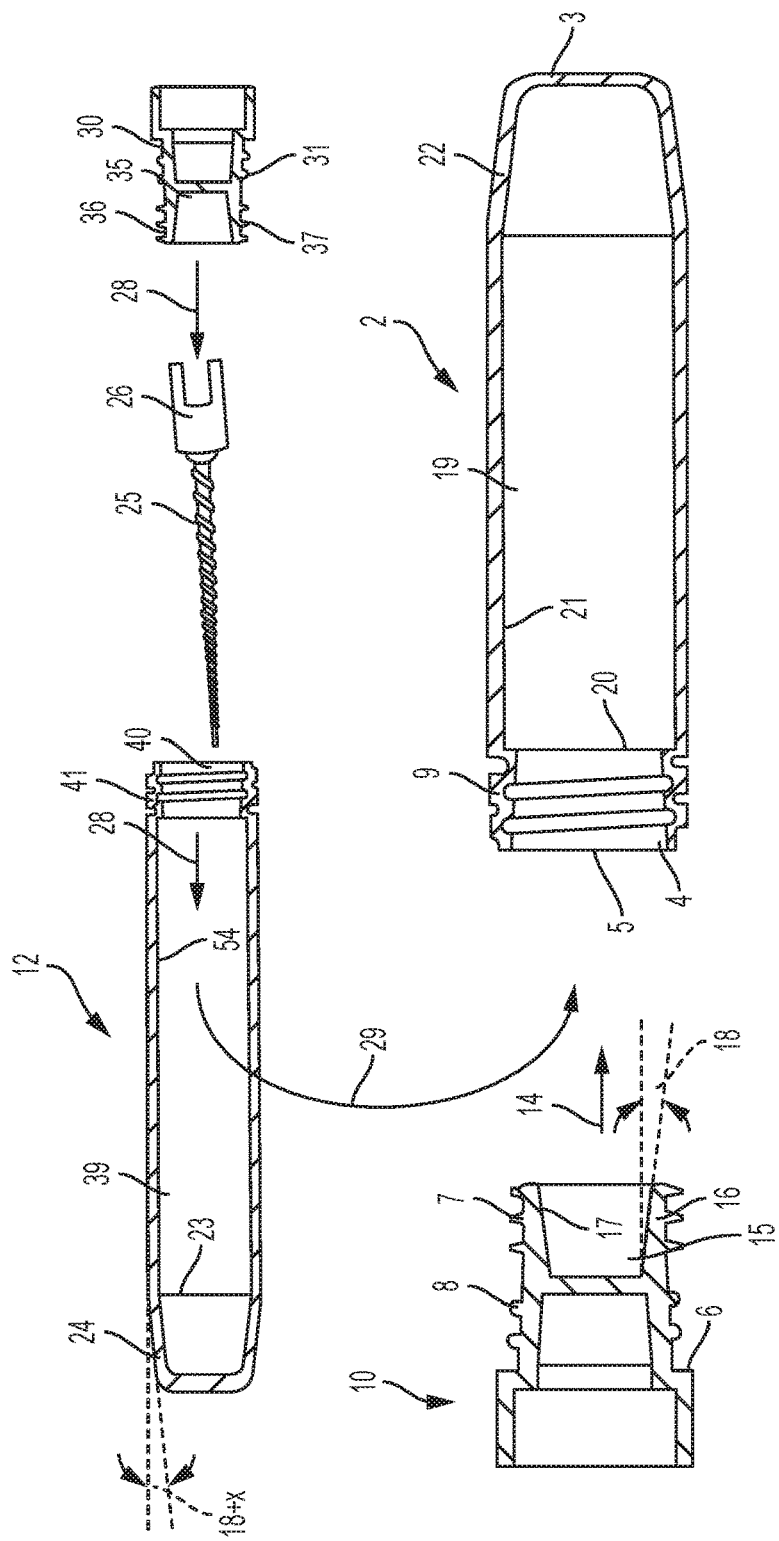
FIG. 2 shows the parts of the exploded diagram in FIG. 1.

FIG. 2 shows all the parts from the exploded diagram in FIG. 1, so that their mutual relationship is discernible.

The sealing closure 30 has a receiving opening 35, which widens conically toward the outside—in the same way as the sealing closure 10. This opening is formed through an annular wall 36, on the outside circumference of which sealing ribs 37 are integrally molded. Here again, the inside circumference of the receiving opening 35 may be smoothed or may be profiled with threads.

The sealing closure 30 is screwed onto the opening side 40 of the inner sleeve 12 in the direction of the arrow 28. It is assumed that the object 25 is already accommodated with its head 26 in the interior 39 of the inner sleeve 12.

In many application cases, it may happen that the diameter of the head 26 of the object 25 is selected so that the head 26 is clamped in the conically widened receiving opening 35, and this receiving opening 35 is spread radially outward so that the sealing ribs 37 press against the inside circumference 54 of the of the inner sleeve 12 with an increased contact pressure.

FIG. 1 thus shows that the length of the inner sleeve 12 is selected so that its sealing closure 30 is supported on the bottom side 3 of the outer sleeve 2 in the interior 19, and the length 43 (see FIG. 3) of the inner sleeve 12 is selected so that the conically tapering bottom sleeve 22 of the inner sleeve 12 penetrates into the outer sleeve 2 in the direction of the arrow 14, into the receiving opening 15 in the sealing closure 10 and executes an expansion movement directed in the radial direction of the arrow 13, forcing the peripheral annular wall 16 radially outward in the direction of the arrow 13 in the sealing closure 10 and pressing the sealing ribs 7 against the inside circumference 21 of the outer sleeve 2 under an increased contact pressure.

The multiple successive sealing ribs in FIG. 1 are labeled in general with reference numeral 7. To show that each sealing rib is peripheral and defines a separate sealing chamber 57, 58 in combination with the neighboring sealing rib, the individual sealing ribs are labeled with separate reference numerals. The outermost sealing rib axially is labeled with reference numeral 56, the next sealing rib in the axial direction is labeled with reference numeral 57 and, finally, the following sealing rib is labeled with reference numeral 59.

The sealing ribs 55, 56, 59 that are closed per se on the circumference and the individual sealing chambers 57, 58, which are compressed when an expansion pressure 11 acts in the radial direction of the arrow 13 and the seal on the inside circumference 21 of the outer sleeve 2 is thereby greatly improved.

FIG. 2 shows that it is preferable if the receiving opening 15 has a cone angle 18 in the sealing closure 10 and for the outside circumference of the bottom sleeve 24 of the inner sleeve 12 to have a cone angle 18 that is the same or at least similar.

The cone angle 18 of the sealing stopper 10, 30 and the bottom sleeve 24 of the inner sleeve 12 may however, also differ from one another.

The bottom sleeve 24 of the inner sleeve 12 is thus clamped in the central receiving opening 15 of the sealing closure 10. When the sealing closure 10 is unscrewed out of the outer sleeve 2, the inner sleeve 12 remains clamped in the receiving opening 15.

The expansion pressure thereby generated is labeled with reference numeral 11 in FIG. 1.

FIG. 1 also shows that the inner sleeve 12 is accommodated centrally in a 180° offset position in the interior of the outer sleeve 2 and is supported with its sealing closure 30 on the bottom side 3 of the outer sleeve 2. The sealing closure 30 is constructed in the same way as the sealing closure 10, so that all the preceding descriptions for the sealing closure 10 also apply to the structure of the sealing closure 30.

Before reaching the sterile area of the operating room, the inner sleeve 12 is removed from the outer sleeve 2 by opening the sealing closure 10 as shown in FIG. 2. In doing so, the inner sleeve 12 with its bottom sleeve 24 remains clamped in the conical receiving opening 15 of the sealing closure 10 that has been removed. Handling thus involves contact only with the sealing closure 10 but no contact with the inner sleeve 12.

In the sterile area of the operating room, a suitable person will open the sealing closure 30 by unscrewing it from the inner sleeve 12 according to FIGS. 1 and 2, wherein the object 25 to be held is removed from the interior 39 of the inner sleeve. It is either loosely accommodated in the inner sleeve 12 or it is held with its head 26 in a clamping action in the conical inclination 27 in the receiving opening 35.

Figure 3:
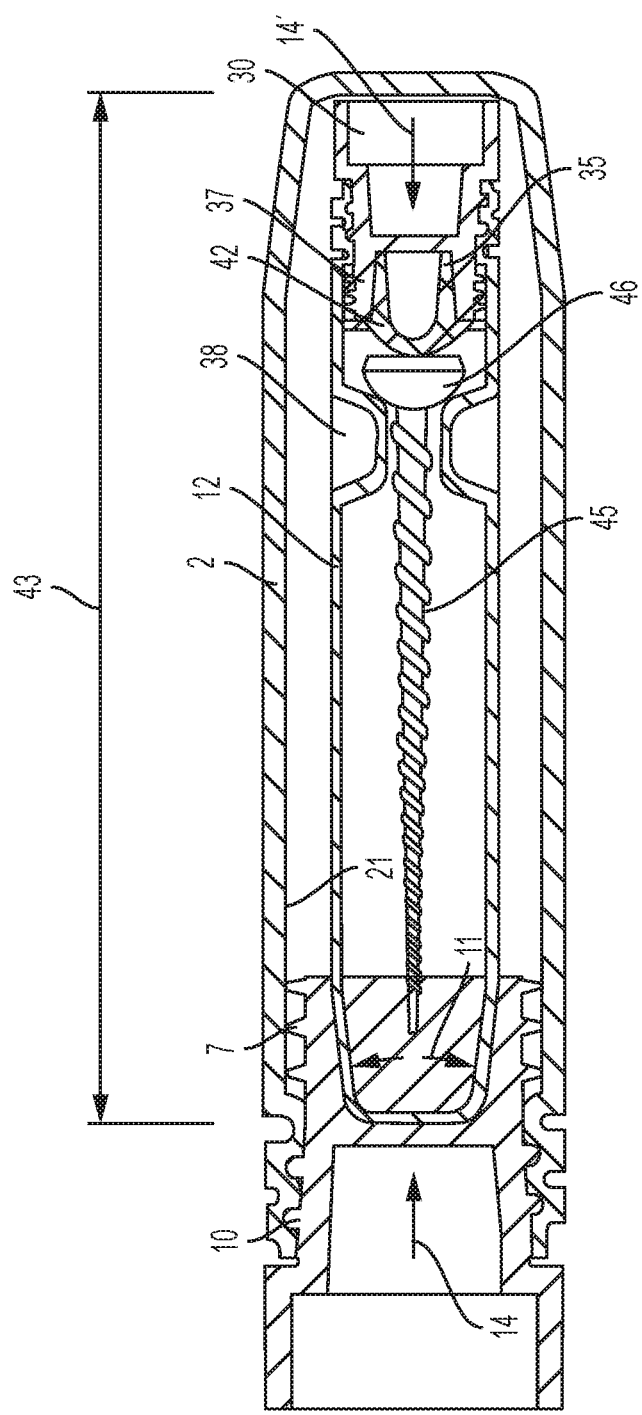
FIG. 3 shows a second embodiment in comparison with FIG. 1.

According to FIG. 3, the head 46 of an object 45 may also be clamped securely against an annular collar 38 having a reduced diameter of the inner sleeve 12 with the help of a pressure piece 42 arranged in the sealing closure 30.

In all three cases, the sterile object 25, 45 can then be removed from the inner sleeve 12 and introduced into the sterile operating field without further contact.

The inner sleeve 12 is constructed in the same way as the outer sleeve 2 and has a shoulder 23 arranged on the bottom side, developing into a bottom sleeve 24, which has a conically tapering diameter.

The bottom sleeve 24 is the expansion member for spreading apart the receiving opening 15 in the sealing closure 10. The inside thread 41 for screwing with the outside thread 31 on the outside circumference of the sealing closure 30 is arranged in the area of the opening side 40.

Furthermore, the sealing ribs 37 arranged on the outside circumference are arranged in the area of the annular wall 36 and are spread apart in the radial direction by the head or by another holding element of the object 25.

Here again, the length of the object 25 is such that it abuts at its front end against the bottom wall of the bottom sleeve 24, so that when the sealing closure 30 is screwed into the inner sleeve 12, the head 26 penetrates into the conically tapering receiving opening 35 and spreads it apart radially from the outside.

In another embodiment, it is of course possible for the length of the object 25 to be selected to be shorter and to provide axial or radial stops in the interior of the inner sleeve, on which the object 25 is stopped in a secured position, so that when the sealing closure 30 is secured into the opening side 40 of the outer sleeve 12, the head 26 penetrates into the conically tapering receiving opening 35 and spreads it apart.

The invention is also not limited to holding an object like a screw, as illustrated in the drawings. Any other instrument or any other object 25 may also be held in the inner sleeve.

In another embodiment, it may also be provided that the length of the object 25 is shorter than the inside length of the inner sleeve 12, so that there need not be any axial or radial stops for the object 25.

In this case, it may be provided that the object 25 with its expansion member (for example, the head 26) is already inserted in advance into the conical receiving opening 35, which is thus already spread open.

Figure 4:
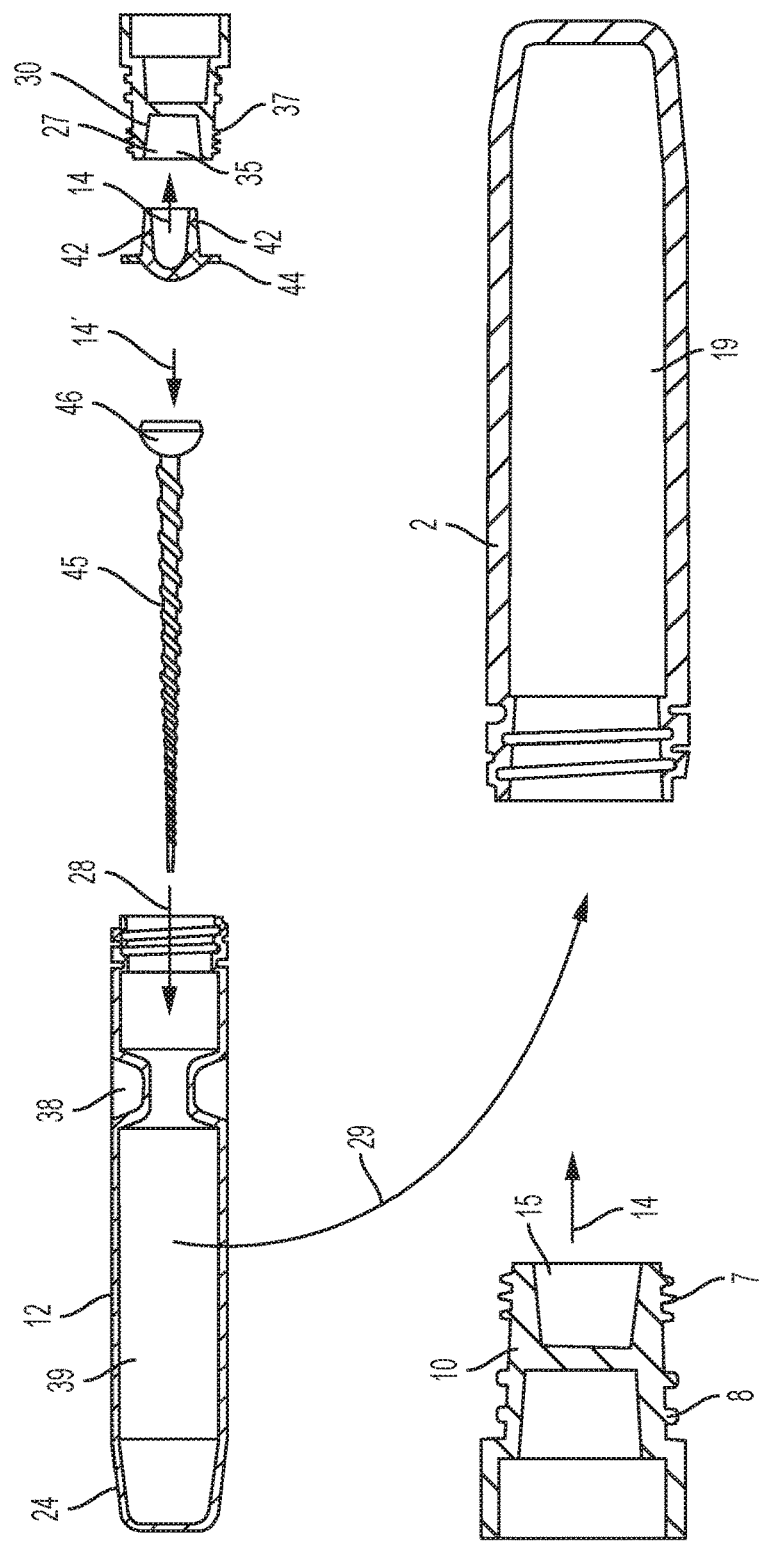
FIG. 4 shows the parts of the exploded diagram in FIG. 3.

In an exploded diagram, FIG. 4 shows and arrangement of a packaging sleeve consisting of an outer sleeve 2 and an inner sleeve 12, in which the object 45 to be packaged together with its head 46 is accommodated on an annular collar 38 of a reduced diameter in the interior 39 of the inner sleeve 12. To protect the object 45 that is to be held in order to prevent movement in the interior 39 of the inner sleeve 12, the object is clamped securely with the help of a pressure piece 42.

On penetration of the object 45 into the inner sleeve 12, the inner sleeve must still be present loosely or may be inserted only as a preliminary matter and with a slight depth of penetration with its pressure piece 42 into the receiving opening 35 of the sealing closure 30. However, as soon as the sealing closure 30 with its outside thread is screwed onto the respective inside thread of the inner sleeve 12, the pressure piece 42 penetrates further into the interior of the receiving opening 35 of the sealing closure 30 in the direction of the arrow 14 until the stop edge 44 that has been widened radially in diameter is in contact with the respective front end of the receiving opening 35. The pressure piece, which preferably has a conical design, thus results in radial expansion of the sealing ribs 37 on penetration into the receiving hole 35 of the sealing closure 30 and in an increased sealing of the sealing closure 30 in the interior of the inner sleeve 12.

As indicated by the arrow 29 in FIG. 4, the inner sleeve 12 that has been completely assembled is then inserted into the outer sleeve 2 with the object 45 now clamped securely under axial pressure, and the total length of the inner sleeve 12, including the completely assembled sealing closure 30, is chosen so that, when the sealing closure 10 is screwed onto the outer sleeve 2, the conically tapering bottom sleeve 24 of the inner sleeve penetrates into the conically widened receiving opening 15 and widens the receiving opening 15 radially, so that the sealing ribs 7 are in contact with the inside of the outer sleeve 2 under an increased contact pressure.

The invention is not limited to the exemplary embodiment shown in FIG. 4 because it may be provided in another embodiment (not shown in the drawings) that the pressure piece 42 is also provided for expansion of the receiving opening 15 in the sealing closure exactly as described above with reference to the inner sleeve 12.

Then, in this case, the conical bottom sleeve 24 of the inner sleeve 12 will not engage in the receiving opening 15 but instead a pressure piece 42 is then partially inserted into the receiving opening 15 and this pressure piece 42 penetrates completely into the receiving opening 15 of the sealing closure 10 when the sealing closure 10 is screwed on and it also widens this.

It is thus clarified that not just the bottom sleeve 24 of the inner sleeve can serve as the expansion member for the outer sealing closure 10, but also the sealing closure 10 can be expanded radially by a pressure piece 42 that is not shown in greater detail, as explained in the example according to FIG. 4 on the basis of the sealing closure 30 in combination with the inner sleeve 12.

Figure 5:
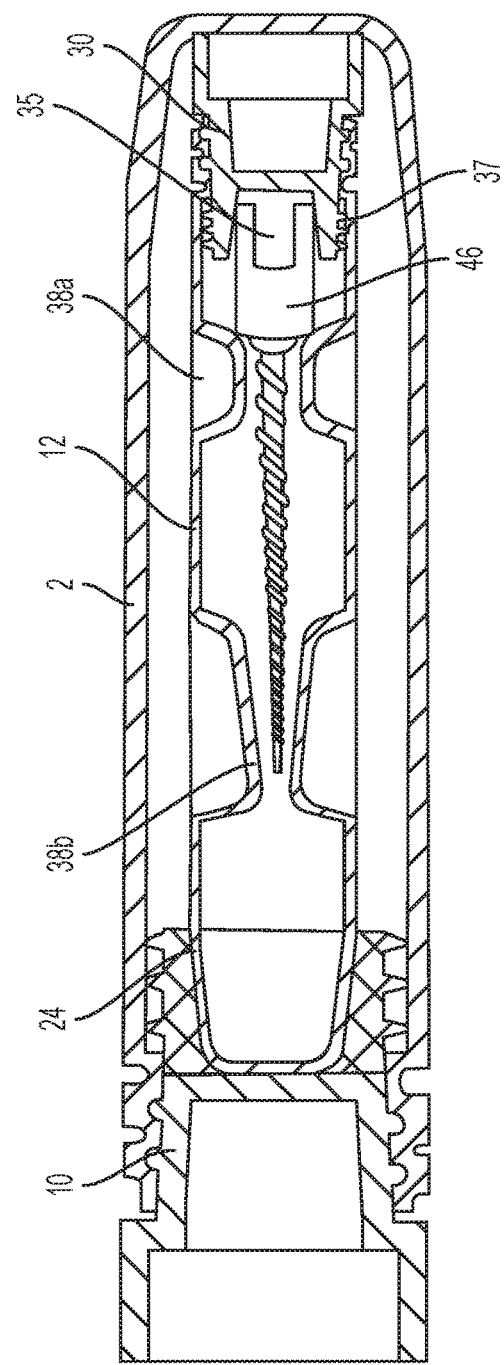
FIG. 5 shows a third embodiment in comparison with FIG. 1.

FIG. 5 shows an exemplary embodiment that has been modified in comparison with FIG. 4, in which it is shown that the head 46 of an object to be held is also suitable directly as an expansion member for expansion of the receiving opening 35 in the sealing closure 30 near the inner sleeve.

The same explanations otherwise apply to the same parts as those shown in FIG. 4.

FIG. 5 also shows the penetration of the bottom sleeve 24 according to FIG. 4 in to the receiving opening 15 of the outer sealing closure 10. FIG. 4 shows the exploded diagram, while FIG. 5 shows the diagram of the device after being completely assembled, wherein the sealing ribs 7 are now pressed against the inside circumference of the outer sleeve 2 under the expansion effect of the conical bottom sleeve 24 with an increased contact pressure.

Figure 7:
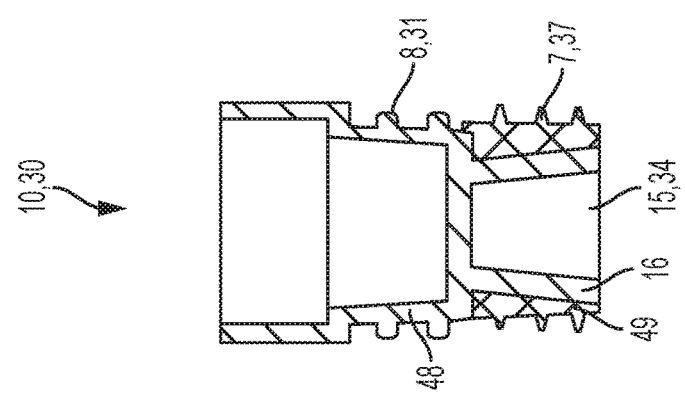
FIG. 7 shows a section through a sealing closure in a second embodiment.
Figure 6:
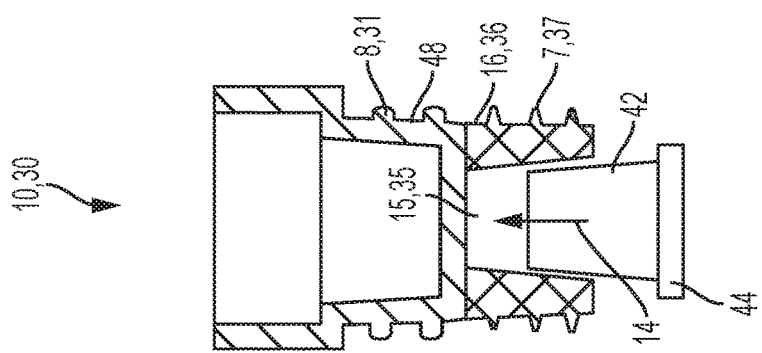
FIG. 6 shows a section through a sealing closure in a first embodiment.

FIGS. 6 and 7 show different embodiments of a sealing closure, wherein each sealing closure can be used either for the outer sealing closure 10 and/or for the inner sealing closure 30.

FIG. 6 shows the penetration of a pressure piece 42 with a conical part into the conically widened receiving opening 15, 35 of the sealing closure 10, which is designed in two parts in the exemplary embodiment shown here.

The annular wall 16, 36, which has the sealing ribs 7, 37, is made of a softer plastic material than comparatively the screw part 48, which is situated above it and has the outer thread 8 and/or 31.

The sealing closure 10, 30 shown in FIG. 6 thus consists of two plastic materials bonded together in one piece at the factory, wherein the plastic of the radially spreadable annular wall 16, 36 consists of a softer plastic material than comparatively the plastic of the screw part 48 arranged above it.

In modification of the embodiment according to FIG. 6, FIG. 7 shows that the entire sealing closure 10, 30 may consist of a harder plastic, which also extends into the annular wall 16 in the hard embodiment.

However, a softer sealing sleeve 49 is integrally molded on or inverted over the outside circumference of the annular wall 16, the sealing ribs 7, 37 that are deformable under a radial expansion pressure being arranged on the outside circumference of the wall.

Figure 8:
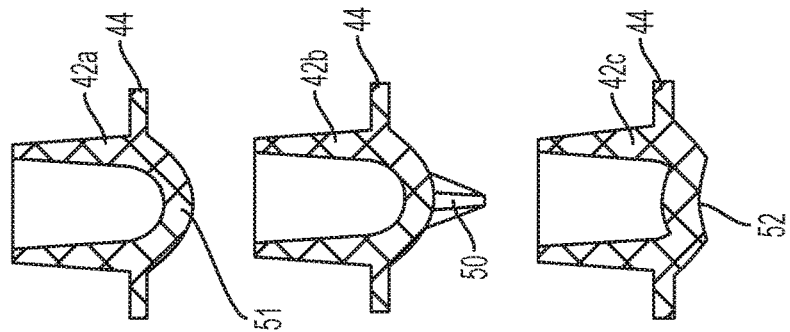
FIG. 8 shows a section through a pressure piece in three different embodiments.

FIG. 8 shows three different embodiments of a pressure piece 42 whose function was already explained with reference to FIG. 4.

The shaping of the pressure piece, in particular its bottom side, depends mainly on the type of head 46 of an object 45 to be clamped with the aid of the pressure piece 42.

In the upper diagram according to FIG. 8, the pressure piece 42a is furnished with a curved surface 51, which is directed outward with a convex shape and exerts a uniform contact pressure on the head 46 of the object 45 to be held—according to FIG. 4.

In the second diagram in FIG. 8 the pressure piece 42b is furnished with a tip 50, which penetrates into a respective hole (not shown) in the central area of the head 46 of an object 45 and thus ensures additional centering for an object 45 to be held in the area of the inner sleeve 12.

The same centering is obtained due to the concave surface 52 of the pressure piece 42c in FIG. 8 because a head surface adapted thereto can also be centered on this concave surface.

FIGS. 9 and 10 show different designs of the sealing ribs 7, 37 of a sealing closure 10, 30. It is assumed in FIG. 9 that the sealing closure consists of the upper screw part 48 and the lower sealing part 53 on the outside circumference of which the different profile shapes of sealing ribs 7, 37 are integrally molded.

It is shown in the upper diagram in FIG. 10 that the expansion pressure 11 of an expansion member acts on the inside circumference 54 of the sealing part 53 in the direction of the arrow 13 and thus leads to a radially outward directed deformation of the sealing ribs 7, 37, because these sealing ribs undergo uniform radially inward deformation under the influence of a counterpressure 32 by contact with the inside circumference of the outer sleeve 2 and/or the inner sleeve 12. The approximately uniformly symmetrical and triangularly profiled sealing ribs 7, 37 are therefore also deformed uniformly under the influence of the counterpressure 32 as shown at the upper left of FIG. 10 on the basis of the sealing rib 7'.

In the central diagram on the left side of FIG. 10, the sealing ribs 7a, 37a are already designed with a curvature and are therefore flattened under the influence of a counterpressure acting inwardly directed and are in contact specifically with large area sealing surfaces on the inside circumference of the outer sleeve 2 or the inner sleeve 12.

The lower diagram on the left side in FIG. 10 shows that the front side of the respective sealing ribs 7b may also be flattened and not zigzag-shaped as shown at the top of FIG. 10 so the result is a different deformation geometry under the influence of the counterpressure 32.

In the diagram at the upper right in FIG. 10, the asymmetrical sealing ribs 7c are also deformed in the direction of the arrow 33 because a counterpressure acts on the respective asymmetrical tip of the sealing rib 7c in the direction of the arrow 32.

In contrast with the diagram at the upper right of FIG. 10, the central diagram shows that the free outer ends of the sealing ribs 7d, 37d may also be designed as tips that become larger toward the outside radially and then flatten under the influence of a counterpressure and thus form linear contact faces on the inside circumference of the outer sleeve 2 and/or of the inner sleeve 12.

The diagram at the bottom of FIG. 10 on the right side shows that it is sufficient to also design the sealing ribs 7e, 37e just with a curvature.

Because of the softness of the elastomeric material used, these curved sealing ribs 7e, 37e are also compressed and unfold straight large area contact faces, establishing a superior sealing effect on the inside circumference of the outer sleeve 2 and/or the inner sleeve 12.

FIG. 11 shows as one exemplary embodiment a modification of the shaping of the outside circumference of the bottom sleeve 24 of the inner sleeve 12.

As indicated in the general description part, in a modified embodiment it may be provided that the outside circumference of the conically tapering bottom sleeve 24 is not designed to be smooth but instead has friction-increasing profile elements.

These profile elements 34a, 34b should permit a controlled removal or controlled extraction of the inner sleeve 12 from the receiving opening 15 in the outer sealing closure 10. When the bottom sleeve is pulled out of the receiving opening 15, a controlled extraction should be possible without any great application of force, and the traction force should be exerted in the most controlled possible manner.

Thus FIG. 11 shows a screw profile 34a on the outside circumference of the conically tapering bottom sleeve 24, so that the inner sleeve 12 is not extracted out of the sealing materials 10 of the outer sleeve with an axial pulling force but instead with a screw-like motion.

Thus a controlled removal of the inner sleeve 12 from the sealing closure 10 of the outer sleeve 2 is possible.

This is also illustrated in FIG. 13 where it is indicated by the use of reference numerals that the same features may also be provided for forming the sealing closure 30, wherein then—in modification of the description above—either the pressure piece 42 of the friction-increasing profiles 34a, 34b or in the case of the design according to FIG. 5, when the head 46 of an object to be held acts directly as an expansion member in the sealing stopper 30, the head 46 is then furnished with the profile shapes 34a, 34b on the outside circumference.

However, for the sake of a simpler description, only the profile shape on the outside circumference of the bottom sleeve 24 of the inner sleeve 12 will now be discussed with reference to FIGS. 11 to 13, although the invention is not limited to this.

In modification of FIG. 11, FIG. 12 shows that, instead of a conically tapering bottom sleeve 24, a cylindrical bottom sleeve, in which the rib profiles 34b that are shown are eliminated first, may also be used. The bottom sleeve is then a smooth cylinder and can also be inserted into the conically tapering receiving opening 15 of the sealing closure 10 with an expansion force.

However, an improved expansion force also occurs when ribs of a larger diameter are arranged on the outside circumference of the cylindrical bottom sleeve 24'.

FIG. 13 shows that it is not essential to the solution to bring the cone angle 18 of the conically tapering bottom sleeve 24 into correspondence with the cone angle 18 of the conically narrowing receiving opening 15.

Figure 14:
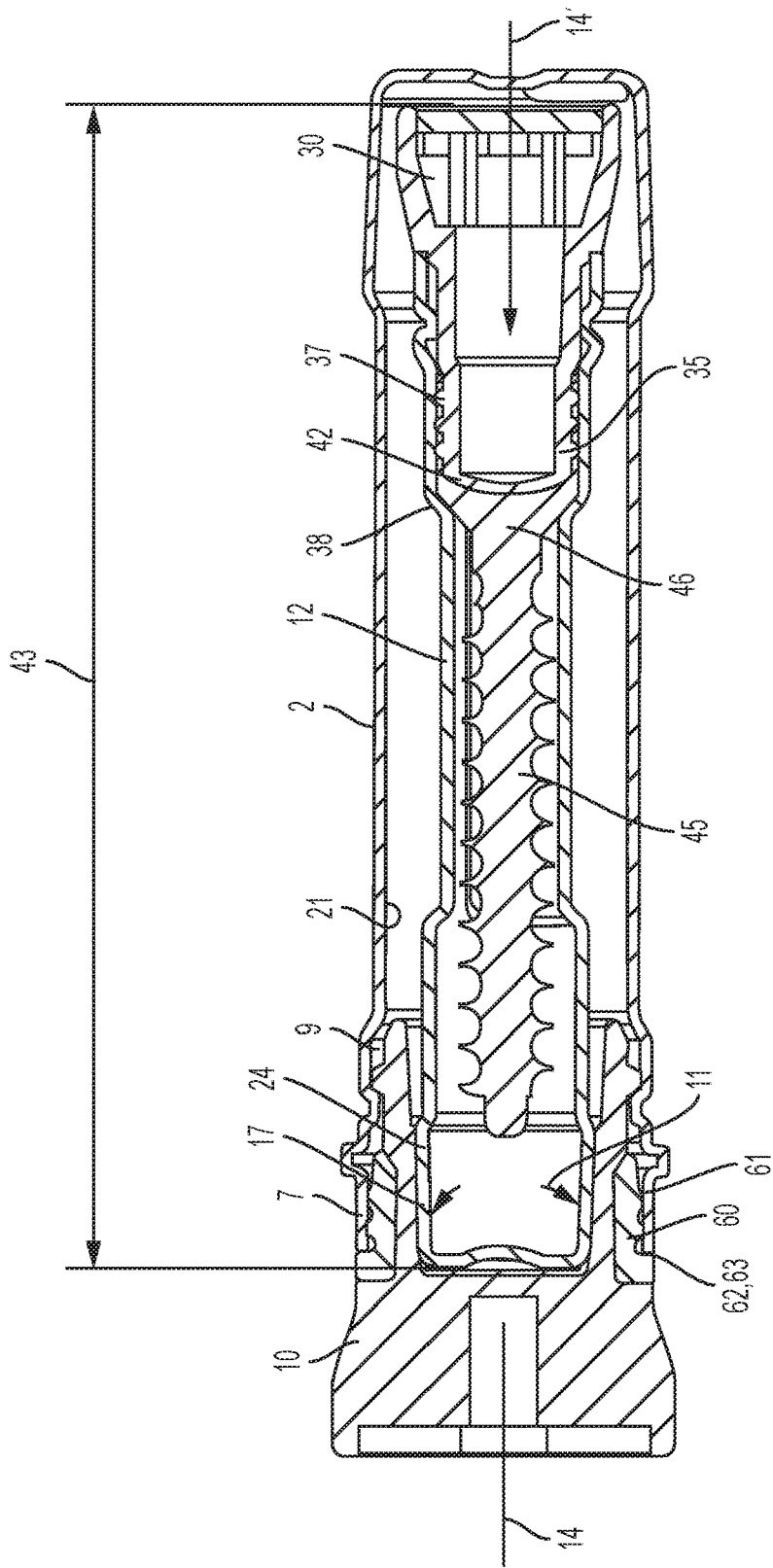
FIG. 14 shows a modified embodiment in comparison with FIG. 1.

The exemplary embodiment according to FIG. 14 has the same sealing closure 30 as that already described in the preceding description on the basis of FIGS. 1 to 13.

The same reference numerals have been used for the same parts. All the explanations and advantages of the first exemplary embodiment are also applicable here.

The main difference between the exemplary embodiment according to FIG. 1 and that according to FIG. 14 is the sealing arrangement on the left side, which now has a special sealing ring 60 according to the invention. However, it is pointed out that the sealing ring 60 and its special sealing functions can also be used in combination with the sealing closure 30 shown on the right side.

The sealing ring 60 may thus be arranged on the left side in FIG. 14 in the sealing closure 10 and/or also on the right side in FIG. 14 in the case of the sealing closure 30, wherein all information about the type or design of the sealing ring 60 also applies to the sealing closure 30 on the right side.

In the exemplary embodiment according to FIG. 14, therefore a higher level sealing arrangement is shown on the left side between the outer sleeve 2 and the stopper-type sealing closure 10 merely for reasons of simplifying the drawing.

This sealing arrangement is characterized in that the sealing closure 10 extends with its sleeve-type end into the interior of the outer sleeve 2, where it forms an outside thread 8, which cooperates with a respective inside thread 9 on the inside of the outer sleeve 2.

It is important that the thread engagement between the threads 8, 9 is shifted axially inward to the interior of the outer sleeve 2 and axially outward the sealing arrangement is now formed on the left side of the thread arrangement 8, 9.

The thread engagement between the respective threads 8, 9 is selected so that a defined locking position is achieved in a certain rotational position, so that this ensures that the stopper-type sealing closure 10 is always screwed with its outside thread 8 into the respective inside thread 9 of the outer sleeve 2 in the same positional and rotational orientation.

The exemplary embodiment according to FIG. 14 is characterized in that, due to the fact that the two respective threads 8, 9 are screwed together, the result is a first axial sealing location 62, which is arranged on the free outer end of a sealing sleeve 61, which is connected to the wall of the outer sleeve 2 in one piece at the factory.

The sealing location 62 is thus formed by the front end of the sealing sleeve 61 on the outside wall end and a sealing ring 60, wherein the sealing ring 60 forms an axial stop at the sealing location 62 and thus forms the sealing location 62.

Due to the two threads 8, 9 being screwed together, thus a first axial seal is established at the sealing location 62.

The sealing location 62 is thus formed by an axial stop 63 in the area of the sealing ring 60.

Figure 15:
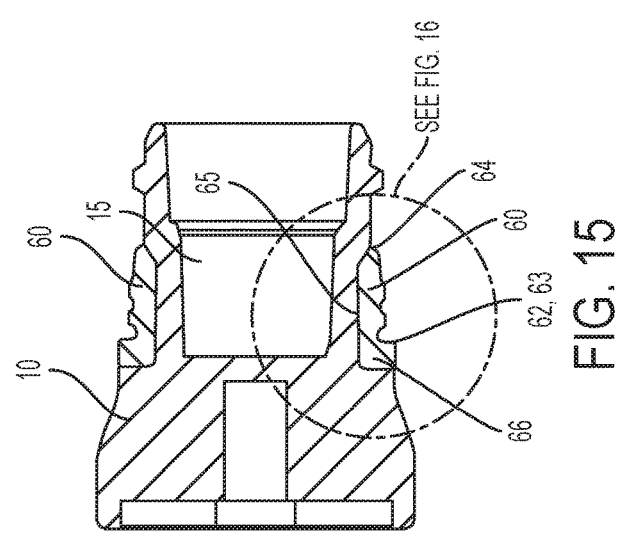
FIG. 15 shows an enlarged diagram of a stopper-type sealing closure showing the arrangement of the novel sealing ring according to FIG. 14.

In the exemplary embodiment according to FIG. 15, which is an enlarged diagram of the view in FIG. 14, it can be seen that the sealing ring 60 is a part with an approximately L-shaped profile, i.e., it has a conical front area 64 that tapers to a point.

Furthermore, there is also an inside stop face 65, which is designed to be approximately cylindrical in the exemplary embodiment shown here.

Apart from that, the sealing ring 60 forms an axial ring stop 66, which is in contact with a respective axial contact face on the head of the stopper-type sealing closure 10.

Figure 16:
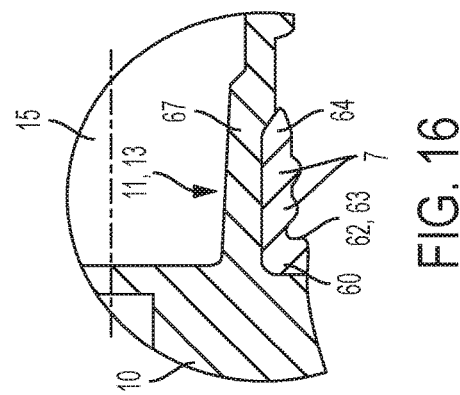
FIG. 16 shows a detailed diagram according to FIG. 15.

According to FIG. 16, the end stop 63 is shifted as far as possible toward the left in the axial direction into the area of the sealing closure 10, while now the sealing ribs 7 that are directed radially outward, as described previously, are in contact with this axial stop 63 on the right side in the axial direction.

The sealing ribs are each approximately round, profiled, ribbed bodies, which are molded in one piece at the factory using the material of the sealing ring 60 and have grooves that narrow the cross section between them.

All other embodiments, such as those mentioned in the description of FIG. 10 ff., are of course also claimed according to the invention.

As described above, an expansion pressure 11, which is directed radially outward, then acts on the inner sleeve 12 in the direction of the arrow 13 in the interior of the conical inclination 17 of the inner sleeve 12 and is thus transferred in the radial direction via the sleeve wall 67 of the stopper-type sealing closure 10 to the novel sealing ring 60, which is thus in sealing contact with the inside circumference of the outer sleeve 2 in two mutually orthogonal directions.

This ensures that the tight and sterile region is shifted as far to the outside as possible into the sealing ring 60 in the axial direction, because the sealing location 62 is situated at the farthest possible axial outer position of the sealing ring 60 and only then—following that in the axial direction—is it connected to the sealing ribs 7 provided for the radial seal.

This is in contrast with the exemplary embodiment according to FIG. 1 because in this embodiment and unprotected inner region of the outer sleeve is present outside of the sealing area and is no longer present in the exemplary embodiment according to FIG. 14 ff.

Figure 17:
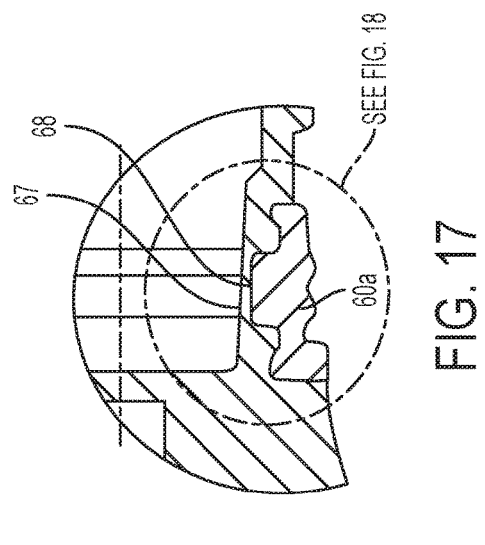
FIG. 17 shows a modified embodiment of the sealing ring in comparison with FIGS. 15 and 16.

In the exemplary embodiment according to FIG. 17, a different form of the sealing ring 60 is proposed, identified here as sealing ring 60a.

This exemplary embodiment is characterized in that the sealing ring 60a no longer has a cylindrical contact face 65 but instead this contact face 68 is now designed with a structure.

The structured contact face results in a reduction in the wall thickness 67 in comparison with FIG. 16, which shows clearly that the spring action of the sleeve wall 67 is increased and it is more capable of transferring the expansion pressure 11 exerted in the direction of the arrow 13 to the sealing ring 60a, which thus experiences a much greater deformation in the radial direction outward.

The sealing pressure and the sealing effect of the sealing ring 60a are thus also improved in FIG. 17.

Figure 18:
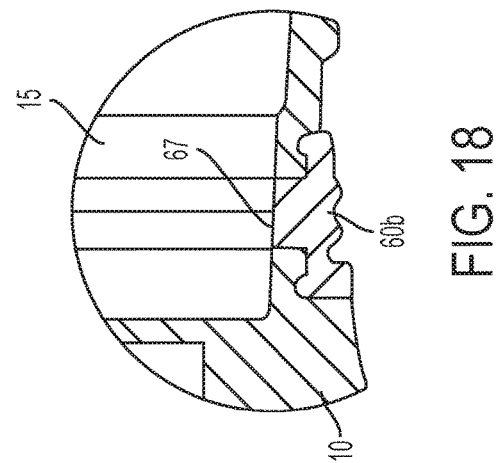
FIG. 18 shows a second modification of the design of the sealing ring.

FIG. 18, in modification of the exemplary embodiment according to FIG. 17, shows a different form of a sealing ring, which is therefore referred to as sealing ring 60b. This exemplary embodiment is characterized in that the sealing ring 60b is molded together with the material of the stopper-type sealing closure 10 as one part in a two-component process as a one-piece part at the factory, but with a different (softer) modulus of elasticity.

It thus forms an integrated body in the sealing closure 10 so that in this exemplary embodiment the sleeve wall 67 is completely omitted and the sleeve wall 67 is then formed by the inside wall of the sealing ring 60b itself.

This ensures that the expansion pressure 11 is exerted directly on the inside wall of the sealing ring 60b in the direction of the arrow 13, so the sealing ring is particularly sensitive to deformation directed radially outward.

Figure 19:
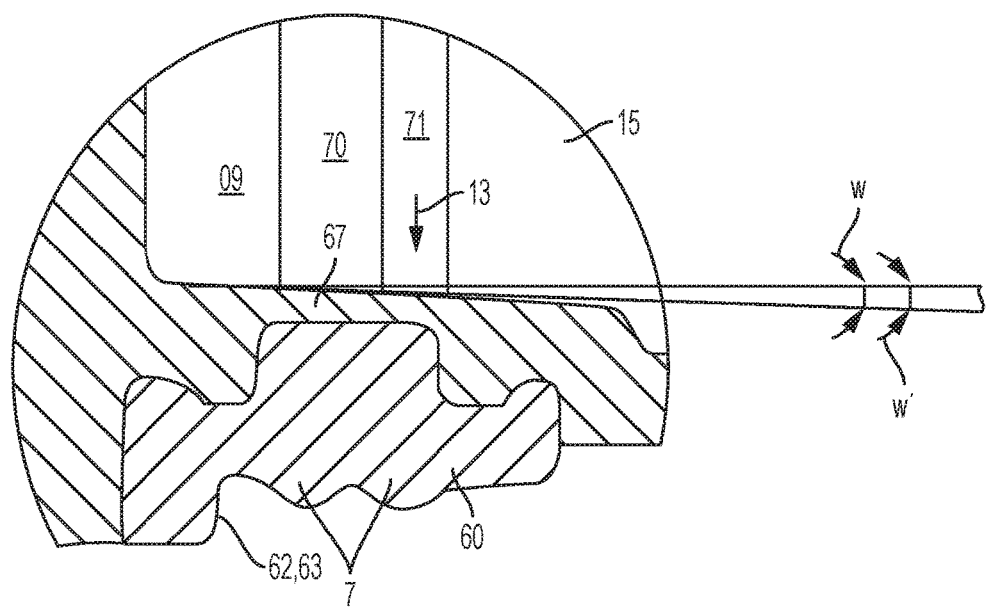
FIG. 19 shows a detailed diagram of the design of the sealing ring according to FIG. 17.

FIG. 19 shows the exemplary embodiment according to FIG. 17 in an enlarged diagram where it can be seen that the sleeve wall 67 is designed as a double cone.

The exemplary embodiments according to FIGS. 19 and 17 thus agree with regard to the fact that there is a double-conical receiving opening 15. It consists of a first conical part 69, a cylindrical part 70 and another conical part 71 connected thereto in the axial direction. Accordingly, the sleeve wall 67 is designed with gradations with respect to the wall thickness in its axial extent.

According to the diagram in FIG. 19, the sleeve wall is initially designed with a conical taper, namely by the cone angle W and then it is designed to be cylindrical with a cylindrical part 70 and again forms a conical part 71 in the axial extension beyond the cylindrical part 70, this cone part also having the cone angle W', where W' is greater than W.

Due to this double-conical design (W cylinder W'), this yields the advantage that the expansion pressure in the direction of the arrow 13 is transferred in particular to the internal area of the sealing ring 60, especially in the areas 70 and 71, and thus there is a concentration of the expansion pressure in the direction of the arrow 13 on the inside circumference of the sealing ring 60, which is therefore deformed radially outward only essentially in this area, while the axial sealing location 62 remains unaffected by this expansion pressure, which is directed radially outward.

This ensures that the sealing force acts mainly on the radial sealing ribs 7 and less on the axial sealing location 62.

It is possible to provide that the cone angle 18 deviates from the cone angle of the bottom sleeve 24 by an amount X (which is a positive or negative even number).

In all application cases, this results in the desired expansion of the radially deformable sealing part 53, on the outside circumference of which the elastomerically deformable sealing ribs 7, 37 are integrally molded.

LEGEND TO THE DRAWINGS

1 Packaging sleeve
2 Outer sleeve
3 Bottom side
4 Opening side
5 End side
6 Stop edge
7 Sealing ribs
8 Outside thread
9 Inside thread
10 Sealing closure (of 2)
11 Expansion pressure
12 Inside sleeve
13 Direction of arrow
14 Direction of arrow
15 Receiving opening (of 10)
16 Annular wall
17 Cone inclination
18 Cone angle
19 Interior (of 2)
20 Shoulder
21 Inside circumference (of 2)
22 Bottom sleeve (of 2)
23 Shoulder
24 Bottom sleeve (of 12)
24' Bottom sleeve
25 Object
26 Head (of 25)
27 Cone inclination
28 Direction of arrow
29 Direction of arrow
30 Sealing closure (of 12)
31 Outside thread (of 30)
32 Counterpressure
33 Direction of arrow
34a Screw profile
34b Rib profile
35 Receiving opening (of 30)
36 Annular wall (of 30)
37 Sealing ribs (of 30)
38 Ring collar (of 12)
39 Interior (of 12)
40 Opening side
41 Inside thread (of 12)
42 Pressure piece (of 30)
43 Length (of 12)
44 Stop edge
45 Object
46 Head (of 45)
47 Annular wall (of 42)
48 Screw part (of 10, 30)
49 Sealing sleeve (of 10, 30)
50 Tip (of 42)
51 Curved surface (of 42)
52 Concave surface (of 42)
53 Sealing part
54 Inside circumference
55 Sealing rib
56 Sealing rib
57 Sealing chamber
58 Sealing chamber
59 Sealing rib
60 Sealing ring a, b
61 Sealing sleeve
62 Sealing location (axial)
63 Stop (axial)
64 Front area (of 60)
65 Stop face
66 Annular stop
67 Sleeve wall
68 Contact face

What is claimed is:

1. A packaging sleeve for storing sterile objects, the packaging sleeve comprising:
    at least one outer sleeve open at a first end that is sealable with a first sealing closure; and
    an inner sleeve accommodated in a first clamping seating in a receiving opening in the first sealing closure of the outer sleeve so that the inner sleeve is positioned within the outer sleeve,
    wherein the first clamping seating presses sealing ribs arranged on an outside circumference of the first sealing closure against an inside circumference of the outer sleeve under increased contact pressure when the inner sleeve is received therein,
    wherein the inner sleeve is open at a first end that is sealable with a second sealing closure and is closed at a second end that is accommodated in the first clamping seating in the receiving end of the first sealing closure of the outer sleeve,
    wherein the second sealing closure has a second clamping seating in a receiving opening thereof, and
    wherein the second clamping seating presses sealing ribs arranged on an outside circumference of the second sealing closure against an inside circumference of the inner sleeve.

2. The packaging sleeve of claim 1, wherein the first sealing closure has the receiving opening on a bottom side thereof, and
    wherein, when the inner sleeve is accommodated within the first clamping seating in the receiving opening, the diameter of a bottom end of the inner sleeve is designed so that on insertion of the bottom end of the inner sleeve into the first clamping seating, the receiving opening is spread radially outward and the sealing ribs arranged on the outside circumference of the first sealing closure are in contact with the inside circumference of the outer sleeve under the increased contact pressure.

3. The packaging sleeve of claim 1, wherein material of the first sealing closure in an area of the sealing ribs consists of a soft plastic, and a material in an area of a corresponding thread part on the outer sleeve consists of a hard plastic material.

4. The packaging sleeve of claim 1, wherein the receiving opening of the first sealing closure is designed as a conical opening that becomes wider in an axial direction.

5. The packaging sleeve of claim 1, wherein the first sealing closure comprises a screw part and a sealing part as one piece, and
    wherein the sealing part includes the sealing ribs arranged on an outside circumference thereof.

6. The packaging sleeve of claim 1, wherein the second sealing closure can be screwed into the inner sleeve, inserted into the inner sleeve, or both.

\* \* \* \* \*